United States Patent [19]

Mardh et al.

[11] Patent Number: 4,851,338
[45] Date of Patent: Jul. 25, 1989

[54] METHOD FOR DIAGNOSING THE PRESENCE OF BACTERIA

[75] Inventors: Per A. Mardh, Lund; Sigfrid Svensson, Furulund, both of Sweden

[73] Assignee: Biocarb AB, Lund, Sweden

[21] Appl. No.: 17,633

[22] Filed: Feb. 24, 1987

Related U.S. Application Data

[62] Division of Ser. No. 477,646, Mar. 22, 1983, Pat. No. 4,665,060.

[30] Foreign Application Priority Data

Mar. 22, 1982 [SE]  Sweden ................................. 8201814

[51] Int. Cl.$^4$ ....................... C12Q 1/04; G01N 33/48; C07H 3/04; A61K 31/70
[52] U.S. Cl. ......................................... 435/34; 435/36; 435/882; 435/822; 436/519; 514/53; 514/54; 514/61; 536/17.2; 536/17.9; 536/55.1
[58] Field of Search ........................... 435/34, 36, 253; 536/17.2, 53, 21, 17.9, 16.8, 123, 55.1; 436/519; 514/54, 61, 53

[56] References Cited

U.S. PATENT DOCUMENTS

| | | | |
|---|---|---|---|
| 4,251,515 | 2/1981 | Suami | 536/53 |
| 4,362,720 | 12/1982 | Lemieux et al. | 536/17.2 |
| 4,657,849 | 4/1987 | Källenius et al. | 536/123 X |
| 4,665,060 | 5/1987 | Märdh et al. | 514/61 |
| 4,724,205 | 2/1988 | Karlsson et al. | 536/53 X |

OTHER PUBLICATIONS

Leffler et al., FEMS Microbiology Letters 8 (1980) pp. 127–134.

Ratcliffe et al., Carbohydrate Research, 93 (1981), pp. 35–41.
Chemical Abstract 89:213042.
Biological Abstract 63: 44794.

Primary Examiner—Robert J. Warden
Assistant Examiner—Carol A. Spiegel
Attorney, Agent, or Firm—Burns, Doane, Swecker & Mathis

[57] ABSTRACT

A composition for therapeutic or diagnostic use in regard to pathogenic microorganisms, containing as an active constituent a structural element having the formula:

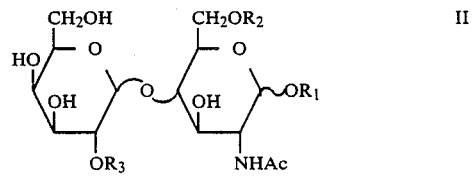

wherein $R_1$, $R_2$, $R_3$ and $R_4$ are same or different and are hydrogen or an organic residue, for example lower alkyl, lower acyl, or a carbohydrate residue or an inorganic residue, such as sulphate or phosphate, and wherein $OR_1$ is in $\alpha$- or $\beta$-configuration; a process for therapeutic treatment; a process for identification or quantification of the said structural element in native biological material; a process for purifying acceptor structures of bacteria; and a process for performing disinfection on surfaces.

16 Claims, No Drawings

METHOD FOR DIAGNOSING THE PRESENCE OF BACTERIA

This application is a division of application Ser. No. 477,646, filed Mar. 22, 1983, now U.S. Pat. No. 4,665,060.

The present invention relates to compositions which are useful for therapeutic treatment of infections as well as prophylaxis and diagnosis in connection herewith. The invention also relates to a process for therapeutic treatment of mammals including man.

The technique according to the invention is applicable to microorganisms of different kinds causing disease, particularly pathogenic bacteria, such as gram-positive cocci, for example streptococci, pneumococci and staphylococci. In particular the invention relates to applications directed to staphylococci, such as *Staphlococcus saprophyticus*, and to bacteria from the genus *Bordetella pertussis* which is the cause of whooping cough. Furthermore, the compositions of the invention have the ability if inhibiting the activity of so-called natural killer cells (NK-cells).

When used in this disclosure the term "microorganism" is intended to cover bacteria and viruses,.

A large number of bacterial infections arise by bacterial attack on mucous membranes. In the initial stage of the course of infection it is essential to the bacteria to have the capability of binding to epithelial cells. The infections ability of bacteria is often directly related to the ability of the bacteria to adhere to epithelial cells. *Staphylococcus saprophyticus* is a bacterium which is frequent cause to urinary tract infections (UTI) mainly in younger women and older men. The bacterium is present on the skin of different animals and is a frequent contamination on meat products. *Staphylococcus saprophyticus* has also been connected with mastitis.

Studies have shown that adhesion of *Staphylococcus saprophyticus* to periurethral cells is caused by a carbohydrate component and that the same carbohydrate component is found in erythrocyte membranes of sheep. This also explains the fact why *Staphylococcus saprophyticus* agglutinates sheep erythrocytes.

The present invention has for its purpose to provide a composition or substance having the ability of replacing the normal receptor function in vivo and in vitro in relation to pathogenic bacteria tending to cause infections in human beings and animals.

Another object of the invention is to provide for such composition or substance that can be used for removal of bacteria from slaughter house products, contaminated surfaces, for example skin, and buildings.

A further object to the invention is to provide a composition or substance that can be used in diagnosis of bacteria.

Yet another object to the invention is to provide a composition or substance that can form the basis for a process for therapeutic or prophylactic treatment of mammals including man.

Another object of the invention is to provide a process for identification and/or quantification of receptor structures, biological material from mammals including man.

Yet another object of the invention is to provide a process for isolation and purification of bacteria or receptor structures of bacteria.

The invention is particularly directed to receptor structures of *Staphylococcus saprophyticus*, but it should be observed that the invention is not limited to this particular bacterium.

Through studies and experiments it has been found that the receptor for *Staphylococcus saprophyticus* on membranes from sheep erythrocytes and urinary epithelium contains the structural element having the formula:

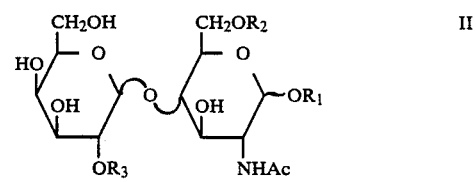

wherein $R_1$, $R_2$ and $R_3$ are same or different and are hydrogen or an organic residue, for example lower alkyl, lower acyl or a carbohydrate residue, or an inorganic residue, such as sulphate or phosphate, and wherein $OR_1$ is in $\alpha$- or $\beta$-configuration.

In this structural formula $R_2$ and $R_3$ in a preferred embodiment are all hydrogen. It is also preferred that group $OR_1$ is present in $\beta$-configuration.

In regard to substituent $R_1$ this may be of any type as long as it does not negatively effect the conditions in relation to the application of the invention. Preferred values of $R_1$ are methyl, or a group having the formula:

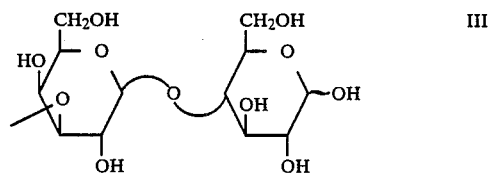

or a group of the formula:

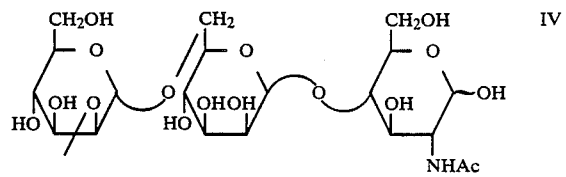

$R_1$ may, of course, also be hydrogen.

Other preferred embodiments of the invention are evident from the appended patent claims and from compounds having the desired receptor function as is presented below in the instant disclosure.

The active ingredients may according to the invention be formulated for use in human or veterinary mdeicine for therapeutic, prophylactic or diagnostic use. In clinical practice the active ingredients will normally be administered topically, orally, or by rectal administration or by injection, in the form of a pharmaceutical preparation comprising the active ingredients, in association with a pharmaceutically acceptable carrier which may be a solid, semi-solid or liquid diluent or an ingestible capsule, and such preparations comprise a further aspect of the invention. The compounds may also be used without carrier material and in solutions for ingestion. As examples of pharmaceutical preparations may be mentioned tablets, drops, suppositories, preparations for topical application such as ointments, jellies, creams, powders, drops and suspensions. Usually the active substance will comprise from 0.05 to 99 % by weight of the preparation, for example from 0.1 to 50 % for preparations intended for oral administration and from 0.5 to 80 % for preparations intended for topical administration. For topical application, especially for application to the urethra opening, the preparations are suitably in the form of an ointment, gel, suspension, or cream. The amount of active substance may vary, for example from 0.5–80% by weight of the active substance. Such preparations for topical application may be prepared in known manner by mixing the active substance with known carrier materials such as isopropanol, glycerol, paraffin, stearyl alcohol, and polyethylene glycol.

To produce pharmaceutical preparations in the form of dosage units for oral application containing a compound of the invention, the active ingredients may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax or other polyethylene glycol waxes compressed to form tablets or cores for dragées. If dragées are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol as a plasticizer, or similar closed capsules, the active substance may be admixed with a Carbowax or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as a physiologically inert plastic substance.

In order to obtain dosage units of oral preparations—tablets and capsules—which are designed so as to prevent release of and possible decomposition of the active substance in the gastric juice, the tablets and dragees may be enteric-coated, that is provided with a layer of a gastric juice-resistant enteric film or coating having such properties that it is not dissolved at the acicid pH in the gastric juice. Thus, the active substance will not be released until the preparation reaches the intestines. As examples of such known enteric coatings may be mentioned cellulose acetate phthalate, hydroxypropylmethyl cellulose phthalates such as those sold under the trade names HP 55 and HP 50, and EUDRAGIT L and EUDRAGIT S.

Effervescent powders may be prepared by mixing the active ingredient with non-toxic carbonates or hydrogen carbonates of e.g. sodium, potassium or calcium, such as calcium carbonate, potassium carbonate and potassium hydrogen carbonate, and solid, non-toxic acids such as tartaric acid, ascorbic acid, and citric acid, and for example aroma.

Liquid preparations for oral application may be in the form of elixirs, syrups or suspensions, for example solutions containing from 0.1% to 20% by weight of active substance, sugar and a mixture of ethanol, water, glycerol, propylene glycol and optionally aroma, saccharine and/or carboxymethyl cellulose as a dispersing agent.

The dosage at which the active ingredients are administered may vary within a wide range and will depend on various factors such as for example the severity of the disorder, the age and weight of the patient, and may have to be individually adjusted. A a possible range for the amount of active ingredients which may be administered per day may be mentioned from 0.1 mg to 5000 mg or from 1 mg to 2000 mg.

The pharmaceutical compositions containing the active ingredients may suitably be formulated so that they provide doses within these ranges either as single dosage units or as multiple dosage units.

The specific compounds described below are all known as such and can be prepared in accordance with known processes. However, the compounds have not earlier been disclosed as possessing properties making them medicinally useful.

The invention also covers a process for therapeutic treatment of mammals including man, an active amount of a composition in accordance with the invention being administered to the mammal.

According to another aspect of the invention there is provided a composition which can be used for identification and/or quantification of the said receptor structure in biological material or to purify bacteria or their acceptor structures. The composition contains one or several structural elements according to the invention as described above or according to the patent claims covalently or otherwise associated to for example a macromolecular carrier, optionally through a coupling arm. Useful carriers may be synthetic or naturally occurring polypeptides, polysaccharides or other types of polymers or particles. This is conventional in the art, see for example refs. 6–10, the contents of which are incorporated herein by reference.

The coupling arm between the structural element and a macromolecular carrier may be any of the following:

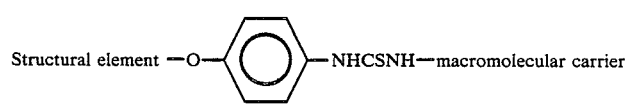

Structural element 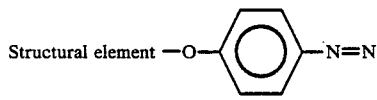

Structural element 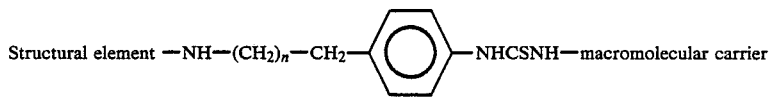

Structural element 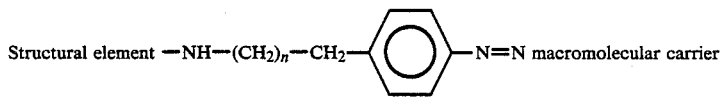

Structural element —NH—(CH$_2$)$_n$—CONH—macromolecular carrier
Structural element —NH—macromolecular carrier In the above examples n may vary between 1 and 15. Preferred structural elements in this type of composition according to the invention are given in the appended patent claims.

Haemagglutination reaction of sheep erythrocytes as caused by *S. saprophyticus* is probably due to interaction between some membrane structure of the surface of the bacterium and receptors of the surface of the sheep erythrocyte containing the said structural element.

The adhesion of *S. saprophyticus* to urinary tract epithelial cells is probably due to interaction between some membrane structure of the surface of the bacterium and receptors of the surfaces of the epithelial cells containing the above said structural element. The invention is, however, not bound by these theories.

The invention will in the following be further described by non-limiting examples.

EXAMPLE 1

Inhibition of haemagglutination of sheep erythrocytes with *Staphylococcus saprophyticus* by the addition of oligosaccharides.

In the tests the bacteria *S. saprophyticus* strains, both isolated from urine from patents having urinary tract infection, were used. The bacteria were cultivated in tryptone broth over night, pelletized by means of centrifugation and washed twice with PBS, pH 7.2. Haemagglutination was performed using erythrocytes from sheep obtained from sheep blood and washed twice with 0.85 % saline.

In the haemagglutination-indication experiments microtitre plates (Limbo Sc. Comp. Inc) were used. 25 μl of bacterial suspension were titrated in PBS by two-step titre steps, 25 μl of 1% erythrocyte suspension being then added. The haemagglutination titre was determined after incubation of the plates for 2–4 hours in room temperature.

In the inhibition experiments serial dilutions of the relevant inhibitor (50 μl/well) and 25 μl of bacterial suspension diluted to contain 2 HU haemagglutinating units of bacteria were used. The plates were incubated for 30 minutes at 37° C., 25 μl of the erythrocyte suspension being then added to each well.

The results are presented in Table 1.

TABLE 1

Inhibition of haemagglutination between sheep erythrocytes and *S. saprophyticus* bacteria (Mc 2 and Mc 194).

| Inhibitor | Minimum inhibitory con. μg/ml |
|---|---|
| β-Galp-(1–4)-GNAc | 300 |
| β-Galp-(1–4)-β-GNAcp-(1–0)-CH$_3$ | 250 |
| β-Galp-(1–4)-β-GNAcp-(1–3)-β-Galp-(1–4)-Glc | 250 |
| β-Galp-(1–4)-β-GNAcp-(1–2)-α-Manp-(1–6)-β-Manp-(1–4)-GNAc (GM$_1$-penta) | 250 |
| β-Galp-(1–4)-β-GNAc-(1–2)-α-Manp-(1–6)⟩β-Manp-(1–4)-GNAc(GM$_1$—octa) β-Galp-(1–4)-β-GNAcp-(1–2)-α-Manp-(1–3)⟩ | 200 |
| β-Galp-(1–3)-β-GNAcp-(1–3)-β-Galp-(1–4)-Glc | >2500 |
| β-GalNAcp-(1–3)-α-Galp-(1–4)-β-Galp-(1–4)-Glc | >2500 |
| α-Galp-(1–4)-β-Galp-(1–4)-Glc | >2500 |
| α-Galp-(1–4)-Gal | >2500 |
| α-Galp-(1–3)-Gal | >2500 |
| β-Galp-(1–3)-β-Galp-(1–3)-Gal | >2500 |
| β-Galp-(1–3)-Gal | >2500 |
| β-Galp-(1–4)-Glc | >2500 |
| Antithrombin III (human) | >2500 |
| Asialoantithrombin III (human) | 250 |
| Transferrin (human) | >2500 |
| Asialotransferrin (human) | 250 |
| Fetuin | >2500 |
| Asialofetuin | 125 |
| α-NeuNAcp-(2–6)-β-Galp-(1–4)-Glc (6'siallyl-lactose) | >2500 |

TABLE 1-continued

Inhibition of haemagglutination between sheep erythrocytes and *S. saprophyticus* bacteria (Mc 2 and Mc 194).

| Inhibitor | Minimum inhibitory con. μg/ml |
|---|---|
| α-NeuNAcp-(2–3)-β-Galp-(1–4)-Glc (3'siallyl-lactose) | >2500 |
| β-Galp-(1–6)-Gal | >2500 |

EXAMPLE 2

Preparation of oligosaccharides from sheep erythrocytes inhibiting haemagglutination of sheep erythrocytes with *S. saprophyticus* bacteria.

For the purpose of investigating whether the structural element tested in Example 1 could be found in sheep erythrocyte membranes erythrocytes from sheep blood were lysed and the membranes were isolated by centrifugation (ref. 4). From 1 liter blood 8 g of membranes were obtained.

To 100 g of lyophilized membranes there are added trifluoroacetic acid anhydride (1 1) and trifluoroacetic acid (1 1), and the reaction mixture is heated to 100° C. in a tube of acid resistant stainless steel at an overpressure of about 4 atms for a period of time of 48 hours.

After this treatment the reaction mixture was cooled and evaporated into dryness, a dark residue being obtained. To the residue methanol (1 1) is added and after 30 minutes evaporation to dryness is performed. The residue is then diluted with 50% aqueous solution of acetic acid (1 1), and the resulting mixture is allowed to stand at room temperature for 1 hour. The reaction mixture is then filtered and evaporated into dryness.

The residue obtained is distributed between water and diethyl ether. The ether phase is washed with water 4 times and the combined water phases are washed with diethyl ether 4 times. The aqueous phase obtained contains the released oligosaccharides.

The oligosaccharide mixture is reduced with sodium borohydride in water in excess and N-acetylated. The oligosaccharide mixture obtained was fractionated on a Sephadex C-25 column in three different fractions. Fraction III containing mono- and di-saccharides and fraction II containing trisaccharides (mainly the carbohydrate fraction of asialo-GM2) did not display an inhibitory ability of the haemagglutination system sheep erythrocytes and *S. saprophyticus*. Fraction I containing oligosaccharides larger than trisaccharides showed inhibiting ability and chemical analysis indicated that this fraction contained inter alia the structural element β-Galp-(1-4)-β-GNAcp-(1-0)- as terminal units in larger oligosaccharide structures. Moreover, a branching site could be detected consisting of a Galp-residue substituted in 3- and 4-position.

EXAMPLE 3

Inhibition of adherence of *S. saprophyticus* to urinary epithelial cells by the addition of oligosaccharides Cells from urinary epithelium were suspended in cell cultivation medium RPMI 1640 (Flow Ltd) to a concentration of $10^5$ cells/ml.

Microorganisms of the type *S. saprophyticus* were suspended in RPMI 1640 to a concentration of $10^9$ bacteria/ml. Oligosaccharides which were tested for their ability of preventing adhesion of *S. saprophyticus* to urinary epithelial cells were dissolved in RPMI 1640 to a concentration of 5 mg/ml. In the experiments 1 ml of the oligosaccharide solution was incubated with 0.1 ml bacterial suspension at 37° C. for 30 minutes. Urinary epithelial cells were incubated with the bacterial suspension incubated in advance as described above with oligosaccharide solution for 45 minutes at 37° C. As a control there was used a bacterial suspension preincubated with 1 ml RPMI 1640.

Incubated samples were filtrated through a 12μ filter and washed 3 times with PBS. The filter was pressed against microscope slides for a few seconds, the slides being then fixed in methanol for 10 minutes. The slides were dried in air and coloured with acridine orange for 2 minutes. The slides were washed, dried in air and studies in fluorescence microscope. The number of bacteria per cell was counted. In each experiment 50 cells were counted.

In these tests it was found that β-Galp-(1-4-)--GNAc, β-Gal-(1-4)-β-GNAc-(1-0)-CH₃ and β-Gal-(1-4)-β--GNAc-(1-4)-β-Gal-(1-4)-Glc reduced the number of adhering bacteria by about 85%, 95% and 96%, whereas β-Galp-(1-4)-Glc did not reduce the number of adhering bacteria in comparison with the control test without oligosaccharides.

EXAMPLE 4

Preparation of compositions containing the structural element in at least bivalent state and covalently linked to a macromolecular carrier The composition was made starting from oligosaccharides having a free reducing end. The reactions used are well known and, therefore, they are only diagrammatically illustrated (in the scheme SR represents the structural element without the sugar residue constituting the reducing terminal, and MB represents a macromolecular carrier).

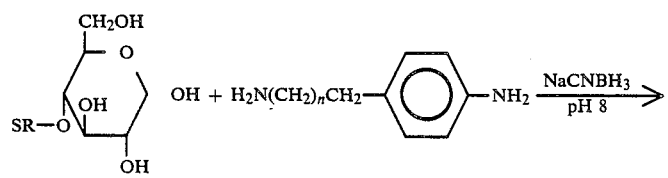

a.

-continued
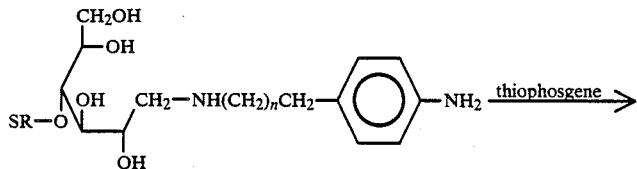
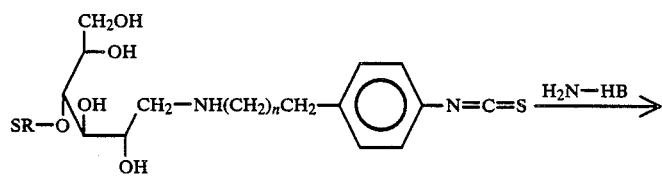
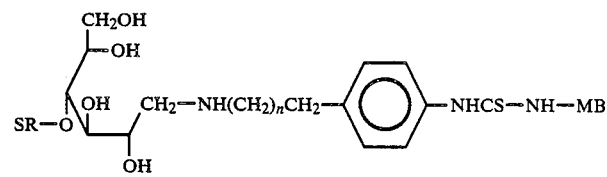
b.
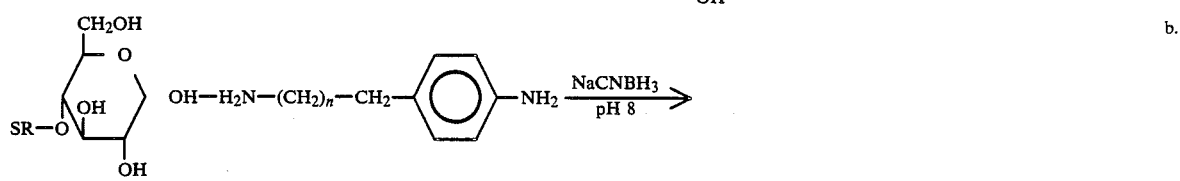
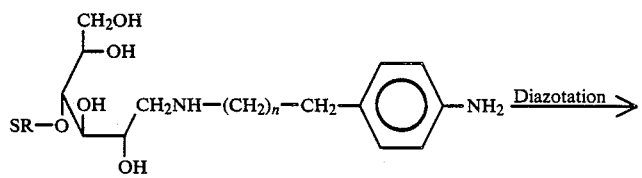
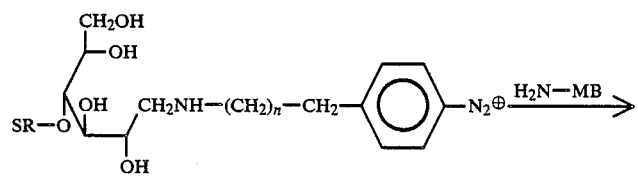
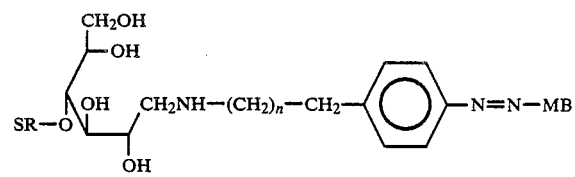
c.
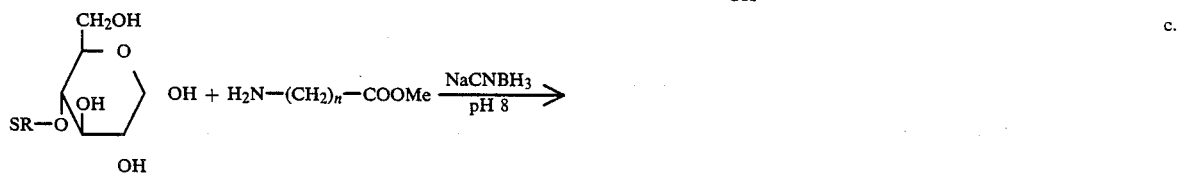
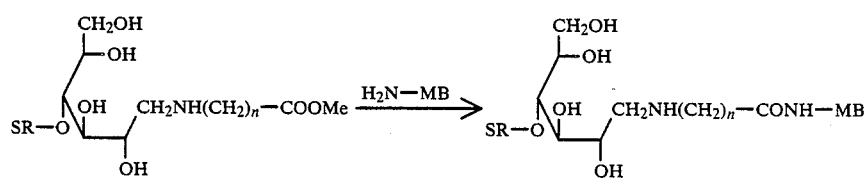

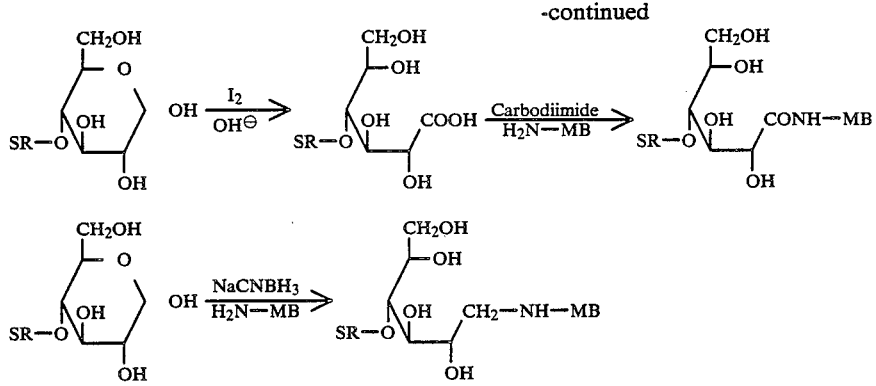

EXAMPLE 5

Preparation of compositions containing the structural element according to the invention in at least bivalent association without covalent bond A glycolipid containing the said structural element is linked by a hydrophobic interaction to lipophilic (hydrophobic) gels, polymers or particles, for example octyl-sepharose, plastics and latex surfaces.

EXAMPLE 6

Preparation of antibodies having specifity against the said structural element a. manufacture of monoclonal antibodies by hybridoma technique I. Balb/c-mice are immunized with a composition according to the invention. The spleen from hyper immunized animals is harvested and a cell suspension is prepared by mechanical comminution of the tissue. After gradient centrifugation to obtain a pure cell preparation the cells are fused by means of polyethylene glycol (PEG, average molecular weight 1500) with established B-myeloma cell lines from Balb/c-mice according to known technique. After cloning the hybridoma cells generating the antibody sought, the cells are propagated on a large scale, the culture medium supernatants being harvested and the antibodies thereof being purified in a conventional manner. For identification of antibody generating clones there is used so-called enzyme-linked immunosorbent assay (ELISA) (Ref 5).

II. Mammals are immunized with an oligosaccharide protein or polymer composition according to the invention. Antibodies are isolated from the hyperimmune serum of the mammal and purified in accordance with conventional techniques.

EXAMPLE 7

Diagnostic test for identification of bacteria having acceptor structures showing specificity towards the structural element according to the invention a. Bacteria are incubated with sheep erythrocytes to agglutinate same. In a parallel test bacteria are incubated with sheep erythrocytes together with the structural element according to the invention at such concentration as to totally inhibit haemagglutination. Haemagglutination and inhibition of haemagglutination is performed according Example 1. Positive haemagglutination of sheep erythrocytes and complete inhibition of haemagglutination after addition of oligosaccharide verifies the fact that the bacteria possess acceptor structure.

b. Bacteria are incubated with a composition wherein the said structural element is convalently or by other association in multivalent form linked to a particular matrix according to Example 4 or 5. Incubation is carried out on microscope slides for 10-15 minutes, the preparation being then studied in a microscope. If the bacteria possess acceptor structure the particles are covered by bacteria. Where the reaction is negative the particles are free from bacteria.

c. Bacteria are mixed with a composition according to Example 4 or 5 on microscope slides positive reaction resulting in agglutination of particles covered with the said structural element.

EXAMPLE 8

Purification of bacteria or acceptor structures a. A composition according to Example 4 or 5 above is arranged in the form of a column. A mixture of bacteria is then passed through the column, bacteria possessing acceptor structures being maintained by interaction with the receptor structures of the column. After rinsing the column can be eluted with buffer containing a receptor-active structural element according to the invention and this results in elusion of bacteria having acceptor structures in a pure form.

b. By a process fully analogous with a. the acceptor structure can be obtained in a pure form.

Bacteria or acceptor structures can be used for the manufacture of vaccines or for determination of antibody in for example body fluids, such as blood, urine or mother's milk.

EXAMPLE 9

Composition for use for disinfection

By disinfection there is meant herein primarily removal of bacteria from a surface, for example a wound.

A 0.1 percent by weight aqueous solution of the compound β-D-Galp-(1-4)-D-GNAc is prepared and applied by using a cotton pad on a surface infected by S. saprophyticus. The solution results in effective removal of the bacterium from the surface.

EXAMPLE 10

Inhibition of haemagglutination of goose erythrocytes with Bordetella Pertussis by addition of oligosaccharides In the tests bacteria of the type Bordetella pertussis newly sampled from an individual suffering from whooping cough were used. The bacteria were cultivated on CFA-agar at +37° C. for 18 hours. The bacterial growth was slurried in PBS, pH 7.2 to a density of $1 \times 10^{10}$ bacteria/ml. Fimbriae from the bacterium were obtained in the following manner:

The bacteria were cultivated on Roux flasks with CFA-agar. After incubation at +37° for 24 hours the bacteria were harvested by adding 10 ml PBS/flask and sterile glass balls. The flasks were shaken and the bacterial suspension removed. The bacteria were pelletized by centrifugation (3000×g, +4°, 30 min.). The supernatant was removed by suction. The bacteria were resuspended in 10 ml PBS and the suspension was treated in a Waring blendor 2 x 20 seconds. The suspension was centrifuged (5000×g, +4°, 30 min.) to pelletize the bacteria. The supernatant containing fimbriae was removed by suction. The bacterial pellet is resuspended, treated in a Waring blender and after centrifugation the supernatant is again recovered. The two supernatants are pooled and ammonium sulphate is added to a concentration of 30 %. After stirring the supernatants are allowed to stand at +4° C. for 18 hours, centrifugation then taking place at 5000 ×g. The supernatant was separated and the precipitation was dialyzed against PBS. The solubilized fimbriae fraction was precipitated with ammonium sulphate once more and dialyzed.

Haemagglutination is performed using erythrocytes from geese (GRBC) suspended to a concentration of 3% v/w in PBS. The agglutination tests were carried out so that 50 μl GRBC were mixed with 2-step dilution of antigen 50 μl bacterial suspension or 50 μl fimbriae suspension and 50 μl PBS in microtitre plates. The plates were sealed with Parafilm and incubated at +44° C. for 4 hours and were then recorded. The last well wherein agglutination could be read by the eye is considered as 1 haemagglutinating unit (1 HU).

In the inhibition experiments there were added instead of PBS 50 μl of an oligosaccharide solution, the inhibiting capacity was studied. The oligosaccharide was tested from the concentration 200 ug/50 μl by 2-step dilution. In the tests there were used concentrations of bacteria and fimbriae which by 3% GRBC results in 2-4 HU. The results are presented in Table II below.

(lymphocytes) for 4 hours at 37° C. The cytotoxic effect is measured as the quantity of isotope released in relation to remaining isotope in the target cells. For details see Malmström, P., Jönsson, Å, and Sjögren, H.O. "Countercurrent distribution of lymphocytes from human peripheral blood in an aqueous two-phase system. II. Separation into subsets of lymphocytes with distinctive functions". Cell Immunol. 53:51–64, 1980. For studying inhibiting substances effector cells ($6 \times 10^6$ cells/ml) are preincubated with the respective oligosaccharides diluted in cultivating medium for half an hour at 37° C. After washing with centrifugation the effector cells are transferred directly to the target cells.

The results obtained are presented in table III below.

TABLE III

% specific cytotoxicity
(ratio 20:1 = 20 × more lymphocytes than target cells)

| Without inhibitor | 1 | 22.3 | | |
| | 2 | 32.0 | | |

| Oligosaccharide | | Minimum inhibitory concentration μg/ml | | |
| --- | --- | --- | --- | --- |
| | | 3 mg/ml | 1 mg/ml | 0.3 mg/ml |
| 3'siallyl lactose[a] | 1 | 20.0 | 25.2 | 23.9 |
| | 2 | 19.1 | 19.7 | 28.7 |
| 6'siallyl lactose[a] | 1 | 9.6 | 15.8 | 21.3 |
| | 2 | 15.1 | 17.2 | 20.2 |
| GM$_1$-penta[a] | 1 | −1.4 | 6.5 | 16.8 |
| | 2 | 0.0 | 2.7 | 13.9 |
| GM$_1$-octa[a] | 1 | 1.7 | 11.3 | 16.1 |
| | 2 | 12.8 | 25.0 | 28.0 |
| Asialofetuin[a] | 1 | 1.5 | 7.0 | 10 |
| | 2 | 1.0 | 5.0 | 15 |

[a] For structures see Table I above.

In the table, the results from two separate experiments are given (1 and 2).

As is clear from the results presented in Table III the cytolytic effect after preincubation with the oligosaccharides GM$_1$-penta, GM$_1$-octa and Asialofetuin in concentrations down to 0.3 mg/ml is inhibited.

Abbreviations
Galp = D-galactopyranosyl
Gal = D-galactose
GNAcp = 2-acetamido-2-deoxy-D-glucopyranosyl

TABLE II

Inhibition of haemagglutination between GRBC and Bordetella pertussis bacteria or fimbriae thereof.

| Inhibitor | Minimum inhibitory concentration μg/ml |
| --- | --- |
| β-Galp-(1–4)-β-GNAc-(1–2)-α-Manp-(1–6)⟩<br>β-Galp-(1–4)-β-GNAcp-(1–2)-α-Manp-(1–3)⟩ β-Manp-(1–4)-GNAc(GM$_1$—octa) | 175 |
| β-Galp-(1–4)-β-GNAcp-(1–2)-α-Manp-(1–6)-β--Manp-(1–4)-GNAc-(GM$_1$-penta) | 675 |
| Asialofetuin | 150 |

EXAMPLE 11

Inhibition of NK-cells activity using oligosaccharides

Lymphocytes isolated from peripheral blood drained from normal donors have the ability of exerting a cytotoxic, (i.e. cell killing activity against certain types of cells in culture. In the instant example there is used a human leukemia cell line called K-562 as a target cell for such cytolytic activity.

Method: K-562 cells intracellularly labelled with radioactive chromium are incubated with effector cells GNAc = 2-acetamido-2-deoxy-D-glucose
Manp = D-mannopyranosyl
GalNAcp = 2-acetamido-2-deoxy-D-galactopyranosyl
Glc = D-glucose
NeuNAcp = N-acetyl-neuraminyl References
Ref. 1. Gibbons, R. J. and Houte. *Ann.Rev.Microbiol.* 29, (1975) 19–44.
Ref. 2. Hovelius, B. Stafylococcus saprophyticus Characteristics, Laboratory diagnosis and involvement in urinary tract infections Dissertation, Lunds Universitet, 1975, Lund, Sweden.

Ref. 3.Mardh, P.-A., Hovelius, B., Hovelius, K., and Nilsson, P.O. Acta vet. scand. 19 (1978) 243-253.

Ref. 4.Dodge, J. T., Mitchell, C., and Hanahan, D. J. Arch. Biochem. Biophys. 100 (1963) 119-130.

Ref. 5.Svenson, S. B. and K. Larsen (1977), J. Immunol. L, part C, 1955.

Ref. 6.Svenson, S. B. and A. A. Lindberg (1979) J. Immunol. Meth. 25, 323.

Ref. 7.Zopf, D. et al (1978) Immunol.Meth.enzymol. L, part C, 163.

Ref. 8.Löngren, J. et al (1976) Arch.Biochem. Biophys. 175, 661.

Ref. 9.Gray, G. R. (1978). In Meth.enzymol.L, part C, 155.

Ref. 10.McBroom, C. R., Samanen, C. H., Goldstein,I. J. In: Methods in Enzymology, Vol28B, ed. V. Ginsburg, p. 212. Academic Press, New York (1972).

We claim:

1. A method for diagnosing the presence of staphylococcus bacteria and bacteria from the genus *Bordetella pertussis* in a mammalian organism comprising reacting a biological sample from a mammalian organism to a compound having the formula:

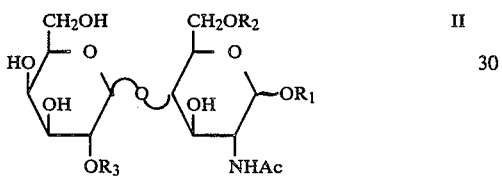

where $R_1$, $R_2$ and $R_3$ are same or different and are hydrogen, lower alkyl, lower acyl, or a carbohydrate residue selected from the group consisting of

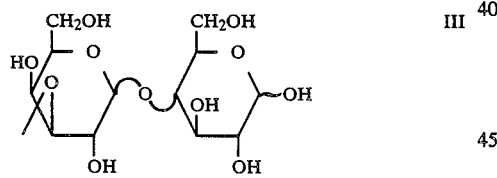

and

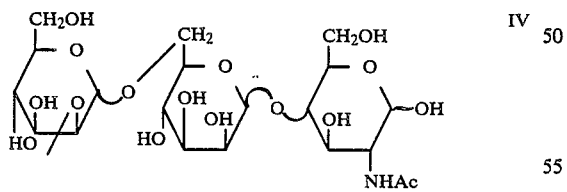

or an inorganic residue selected from the group consisting of sulfate and phosphate, and wherein $OR_1$ is in $\alpha$- or $\beta$-configuration and detecting the presence of staphylococci bacteria or bacteria from the genus *Bordetella pertussis* bound to said compound.

2. A method according to claim 1, wherein said compound $R_2$ and $R_3$ are both hydrogen.

3. A method according to claim 1, wherein said compound $OR_1$ is in $\beta$-configuration.

4. A method according to claim 3, wherein $R_1$ is methyl.

5. A method according to claim 1, wherein $R_1$ is a group having the formula:

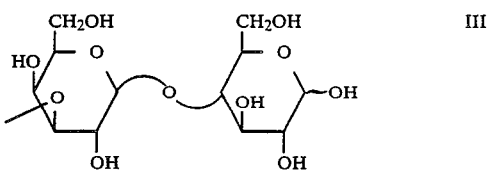

6. A method according to claim 1, wherein $R_1$ is a group having the formula:

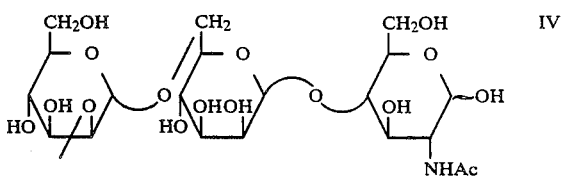

7. A method according to claim 1, wherein $R_1$ is hydrogen.

8. A method according to claim 1, wherein said biological sample contains human epithelial cells.

9. A method according to claim 1, wherein the compound is covalently linked to a macromolecular carrier selected from the group consisting of polypeptide, polysaccharide and polymer, through a coupling arm selected from the group consisting of:

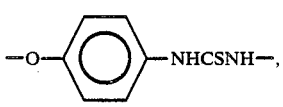

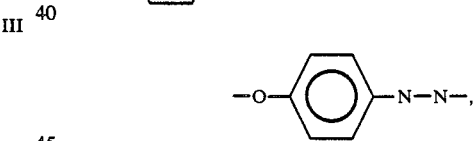

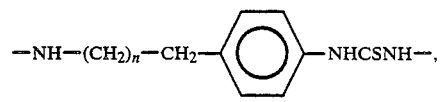

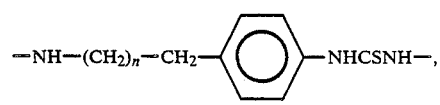

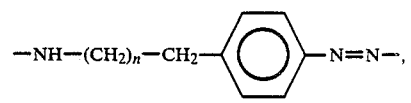

wherein n may vary from 1 to 15.

10. A method for diagnosing the presence of staphylococcus bacteria and bacteria from the genus *Bordetella pertussis* in a mammalian organism comprising reacting a biological sample from a mammalian organism to a compound having the formula:

[Formula II: disaccharide structure with CH2OH, HO, OH, OR3, CH2OR2, OH, OR1, NHAc groups]

wherein R₁, R₂ and R₃ are same or different and are hydrogen, methyl, a carbohydrate residue selected from the group consisting of

[Formula III: disaccharide structure]

and

[Formula IV: trisaccharide structure with NHAc]

or an inorganic residue selected from the group consisting of sulfate and phosphate, and wherein OR₁ is in α- or β-configuration and detecting the presence of staphylococci bacteria or bacteria from the genus *Bordetella pertussis* bound to said compound.

11. A method according to claim 10, wherein said compound R₂ and R₃ are both hydrogen.

12. A method according to claim 10, wherein said compound OR₁ is in β-configuration.

13. A method according to claim 12, wherein R₁ is methyl.

14. A method according to claim 10, wherein R₁ is a group having the formula:

[Formula III]

15. A method according to claim 10, wherein R₁ is a group having the formula:

[Formula IV]

16. A method according to claim 10, whreein R¹ is hydrogen.

* * * * *